United States Patent
Li

(10) Patent No.: US 11,179,090 B2
(45) Date of Patent: Nov. 23, 2021

(54) CONTROL METHOD AND DEVICE BASED ON BRAIN SIGNAL, AND HUMAN-COMPUTER INTERACTION DEVICE

(71) Applicant: BOE TECHNOLOGY GROUP CO., LTD., Beijing (CN)

(72) Inventor: Yingyi Li, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 325 days.

(21) Appl. No.: 16/315,886

(22) PCT Filed: Jan. 8, 2018

(86) PCT No.: PCT/CN2018/071728
§ 371 (c)(1),
(2) Date: Jan. 7, 2019

(87) PCT Pub. No.: WO2019/000901
PCT Pub. Date: Jan. 3, 2019

(65) Prior Publication Data
US 2019/0307352 A1 Oct. 10, 2019
US 2020/0305751 A9 Oct. 1, 2020

(30) Foreign Application Priority Data

Jun. 28, 2017 (CN) .......................... 201710510171.2

(51) Int. Cl.
*A61B 5/375* (2021.01)
*A61B 5/1455* (2006.01)
(Continued)

(52) U.S. Cl.
CPC .......... *A61B 5/375* (2021.01); *A61B 5/14553* (2013.01); *A61B 5/291* (2021.01);
(Continued)

(58) Field of Classification Search
CPC ... A61B 5/0482; A61B 5/7235; A61B 5/0476; A61B 5/0478; A61B 5/048;
(Continued)

(56) References Cited

U.S. PATENT DOCUMENTS 8,155,736 B2 * 4/2012 Sullivan .................. G06F 3/015
600/544
2008/0294033 A1 11/2008 Yamazaki

FOREIGN PATENT DOCUMENTS

CN 1575745 A 2/2005
CN 1577354 A 2/2005
(Continued)

OTHER PUBLICATIONS

Kreilinger, Alex et al. "Switching between Manual Control and Brain-Computer Interface Using Long Term and Short Term Quality Measures." Frontiers in neuroscience vol. 5 147. Jan. 18, 2012, doi:10.3389/fnins.2011.00147 (Year: 2012).*
(Continued)

*Primary Examiner* — Devin B Henson
*Assistant Examiner* — Justin Xu
(74) *Attorney, Agent, or Firm* — Armstrong Teasdale LLP

(57) ABSTRACT

Provided in the embodiments of the present disclosure are a control method and device based on brain signal, and a human-machine interaction device, which periodically acquire EEG signals and cerebral oxygen signals within a target period, generate an electroencephalogram (EEG) wave curve representing changes of the EEG signals and a cerebral oxygen wave curve representing changes of the cerebral oxygen signals respectively within the target period, determine whether the EEG wave curve and the cerebral oxygen wave curve satisfy a condition for controlling a controlled device to perform a target operation, and control the controlled device to perform the target operation
(Continued)

when the EEG wave curve and the cerebral oxygen wave curve satisfy the condition.

19 Claims, 4 Drawing Sheets

(51) Int. Cl.
    *A61B 5/00*         (2006.01)
    *G06F 3/01*         (2006.01)
    *A61B 5/291*       (2021.01)
    *A61B 5/369*       (2021.01)
    *A61B 5/374*       (2021.01)

(52) U.S. Cl.
    CPC .............. *A61B 5/369* (2021.01); *A61B 5/374* (2021.01); *A61B 5/6803* (2013.01); *A61B 5/7235* (2013.01); *G06F 3/015* (2013.01); *A61B 5/0006* (2013.01); *A61B 5/4064* (2013.01)

(58) Field of Classification Search
    CPC . A61B 5/14553; A61B 5/6803; A61B 5/0006; A61B 5/4064; G06F 3/015; G06F 3/0304
    See application file for complete search history.

(56) References Cited

FOREIGN PATENT DOCUMENTS

| CN | 1719385 A | 1/2006 |
|---|---|---|
| CN | 201389013 Y | 1/2010 |
| CN | 101853070 A | 10/2010 |
| CN | 102894971 A | 1/2013 |
| CN | 104182042 A | 12/2014 |
| CN | 104363983 A | 2/2015 |
| CN | 105578954 A | 5/2016 |
| CN | 205340145 U | 6/2016 |
| CN | 206081622 U | 4/2017 |
| CN | 206213376 U | 6/2017 |
| CN | 107137079 A | 9/2017 |

OTHER PUBLICATIONS

PCT International Search Report, Application No. PCT/CN2018/071728, dated Apr. 8, 2018, 9 pages: with English translation.
PCT Written Opinion, Application No. PCT/CN2018/071728, dated Apr. 8, 2018, 6 pages.: with English translation of relevant part.
China First Office Action, Application No. 201710510171.2, dated Mar. 22, 2019, 21 pps.: with English translation.

\* cited by examiner

CONTROL METHOD AND DEVICE BASED ON BRAIN SIGNAL, AND HUMAN-COMPUTER INTERACTION DEVICE

CROSS REFERENCE TO RELATED APPLICATIONS

This patent application is a National Stage Entry of PCT/CN2018/071728 filed on Jan. 8, 2018, which claims the benefit and priority of Chinese Patent Application No. 201710510171.2 filed on Jun. 28, 2017, the disclosures of which are incorporated by reference in their entirety as part of the present application.

BACKGROUND

The present disclosure relates to the field of human-computer interaction technology, and in particular, to a control method and device based on brain signal, and a human-machine interaction device.

There are many active nerve cells (also called neurons) in human brains. Ion current of the neurons generates voltage changes, and such weak bioelectrical change is called brain wave, also electroencephalogram (EEG). In recent years, with the maturity of brain wave acquisition and recognition technology, human-computer interaction devices based on brain wave control have become increasingly active as an emerging experience.

BRIEF DESCRIPTION

Embodiments of the present disclosure provide a control method and device based on brain signal, and a human-machine interaction device.

In a first aspect, an embodiment of the present disclosure provides a control method based on brain signal, including periodically acquiring EEG signals and cerebral oxygen signals within a target period, and generating, according to the acquired EEG signals and cerebral oxygen signals, respectively an EEG wave curve representing changes of the EEG signals and a cerebral oxygen wave curve representing changes of the cerebral oxygen signals within the target period, determining whether the EEG wave curve and the cerebral oxygen wave curve satisfy a condition for controlling a controlled device to perform a target operation, and controlling the controlled device to perform the target operation when the EEG wave curve and the cerebral oxygen wave curve satisfy the condition.

In a possible implementation, in the above control method provided by the embodiment of the present disclosure, controlling the controlled device to perform the target operation when the EEG wave curve and the cerebral oxygen wave curve satisfy the condition includes determining that, within the target period, a brain is in an active state when a numerical increase amount of the EEG wave curve is greater than or equal to a first threshold and a numerical decrease amount of the cerebral oxygen wave curve is greater than or equal to a second threshold, controlling the controlled device to perform an operation corresponding to the active state of the brain, determining that, within the target period, the brain is in a calm state when a numerical decrease amount of the EEG wave curve is greater than or equal to a third threshold and a numerical increase amount of the cerebral oxygen wave curve is greater than or equal to a fourth threshold, and controlling the controlled device to perform an operation corresponding to the calm state of the brain.

In a possible implementation, in the above control method provided by the embodiment of the present disclosure, controlling the controlled device to perform the target operation when the EEG wave curve and the cerebral oxygen wave curve satisfy the condition further includes within the target period, keeping the controlled device performing the operation which is currently performed when a numerical change amount of at least one of the EEG wave curve and the cerebral oxygen wave curve is less than respective target thresholds.

In a possible implementation, in the foregoing control method provided by the embodiment of the present disclosure, determining whether the EEG wave curve and the cerebral oxygen wave curve satisfy a condition for controlling the controlled device to perform a target operation includes extracting an EEG feature of the EEG wave curve and extracting a cerebral oxygen feature from the cerebral oxygen wave curve, fusing the extracted EEG feature and the extracted cerebral oxygen feature, and determining whether the fused feature satisfies the condition for controlling the controlled device to perform the target operation.

In a second aspect, an embodiment of the present disclosure provides a control device based on brain signal including an EEG signal detection apparatus, a cerebral oxygen signal detection apparatus, and a processor, wherein the EEG signal detection apparatus and the cerebral oxygen signal detection apparatus are coupled to the processor respectively, the processor is configured to control the EEG signal detection apparatus to periodically detect EEG signals and control the cerebral oxygen signal detection apparatus to periodically detect cerebral oxygen signals within a target period, generate, according to the detected EEG signals and the detected cerebral oxygen signals, an EEG wave curve representing changes of the EEG signals and a cerebral oxygen wave curve representing changes of the cerebral oxygen signals within the target period respectively, determining whether the EEG wave curve and the cerebral oxygen wave curve satisfy a condition for controlling a controlled device to perform a target operation, and in response to determining that the EEG wave curve and the cerebral oxygen wave curve satisfy the condition, send a control instruction to the controlled device to cause the controlled device to perform a target operation corresponding to the control instruction.

In a possible implementation, in the above control device provided by the embodiment of the present disclosure, the controlled device performing the target operation corresponding to the control instruction when the EEG wave curve and the cerebral oxygen wave curve satisfy the condition includes determining that, within the target period, a brain is in an active state when a numerical increase amount of the EEG wave curve is greater than or equal to a first threshold and a numerical decrease amount of the cerebral oxygen wave curve is greater than or equal to a second threshold, controlling the controlled device to perform an operation corresponding to the active state of the brain, or determining that, within the target period, the brain is in a calm state when a numerical decrease amount of the EEG wave curve is greater than or equal to a third threshold and a numerical increase amount of the cerebral oxygen wave curve is greater than or equal to a fourth threshold, controlling the controlled device to perform an operation corresponding to the calm state of the brain, or keeping the controlled device performing, within the target period, the currently performed operation when a numerical change amount of at least one of the EEG wave curve and the cerebral oxygen wave curve is less than respective target thresholds.

In a possible implementation, in the above control device provided by the embodiment of the present disclosure, the EEG signal detection apparatus includes an EEG detection electrode.

In a possible implementation, in the above control device provided by the embodiment of the present disclosure, the cerebral oxygen signal detection apparatus includes a detection light source, and an optical sensor spaced apart from the detection light source by a target distance, wherein the detection light source is configured to emit infrared light to the cerebral cortex so that the emitted infrared light interacts with the blood oxygen tissue of the cerebral cortex, and the optical sensor is configured to detect the infrared light that has been reflected by the cerebral cortex without interacting with the blood oxygen tissue.

In a possible implementation, in the above control device provided by the embodiment of the present disclosure, the detection light source includes a first light emitting chip and a second light emitting chip which are packaged in a same package structure, a wavelength of infrared light emitted by the first light emitting chip is about 760 nm, and a wavelength of infrared light emitted by the second light emitting chip is about 850 nm.

In a possible implementation, the foregoing control device provided by the embodiment of the present disclosure further includes a first filtering and amplification circuit coupled between the processor and the EEG detection electrode.

In a possible implementation, the foregoing control device provided by the embodiment of the present disclosure further includes a second filtering and amplification circuit coupled between the processor and the optical sensor.

In a possible implementation, the foregoing control device provided by the embodiment of the present disclosure further includes a driving circuit coupled to the detection light source.

In a possible implementation, the foregoing control device provided by the embodiment of the present disclosure further includes a wireless transmission module, configured to send the control instruction from the processor to the controlled device.

In a possible implementation, the foregoing control device provided by the embodiment of the present disclosure is integrated in a headset component.

In a third aspect, an embodiment of the present disclosure provides a human-machine interaction device, including any of the foregoing control device and the controlled device.

DETAILED DESCRIPTION

Figure 1:
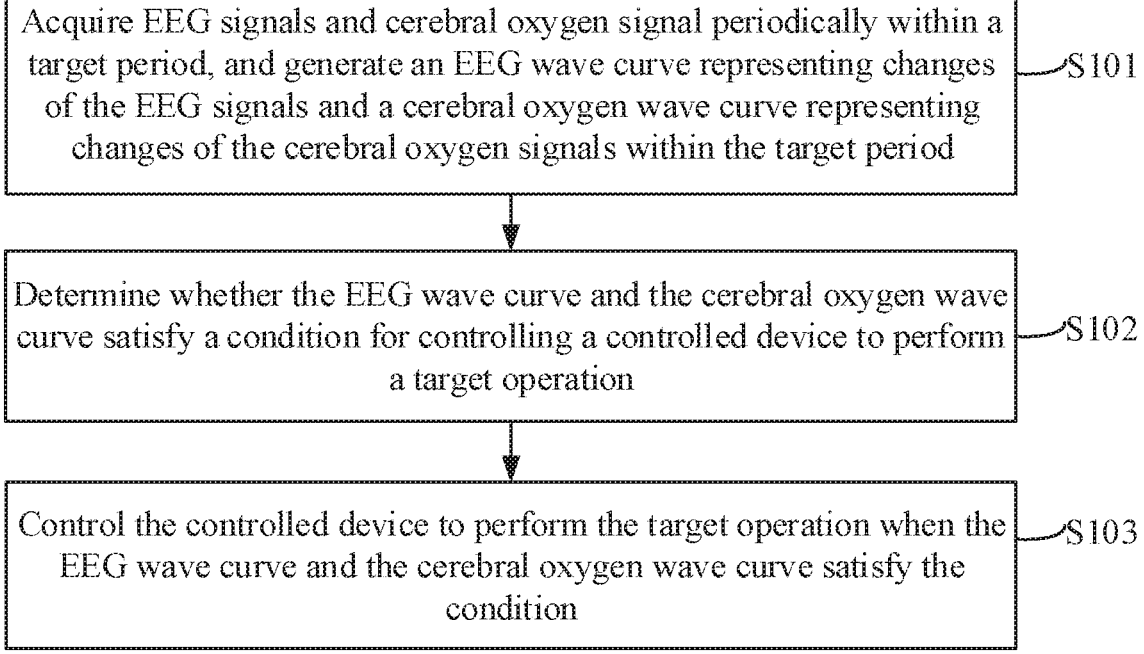
FIG. 1 is a flowchart of a control method based on brain signal according to an embodiment of the present disclosure.

Embodiments of the present disclosure provide a control method and device based on brain signal, and a human-machine interaction device, for improving control accuracy.

In order to make the technical solutions and advantages of the present disclosure more clear and easy to understand, the present disclosure will be further illustrated below in conjunction with the drawings and embodiments. However, the exemplary embodiments may be implemented in a variety of forms and should not be construed as being limited to the embodiments set forth herein; rather, these embodiments are provided to make the disclosure more comprehensive and complete and to comprehensively convey the ideas of the embodiments to those skilled in the art. The same reference numerals in the drawings denote same or similar structures, and repeated description thereof will be omitted. The words expressing position and orientation in the present disclosure are described by way of example in the accompanying drawings, modifications may also be made as needed, and the modifications are included in the protection scope of the present disclosure.

The principle of a human-computer interaction device based on brain wave control is pre-establishing a mapping relationship between brain wave data and an operation instruction for the controlled device, and then, after acquiring brain wave data, determining an operation instruction corresponding to the brain wave data according to the mapping relationship, and at last, instructing the controlled device to execute the operation instruction.

However, since human brain waves change very fast and are prone to hopping in the case of inattention, the operation instruction executed by the controlled device in such cases may be an erroneous or invalid operational instruction. All of the above problems affect the accuracy of the human-computer interaction device when operating, and bring negative effect on user experiences.

First, an embodiment of the present disclosure provides a control method based on brain signal. As shown in FIG. 1, the control method based on brain signal provided by the embodiment of the present disclosure may include the following steps:

S101, acquiring EEG signals and cerebral oxygen signals periodically within a target period (the target period may be preset according to needs of a person skilled in the art), and generating, according to the acquired EEG signals and cerebral oxygen signals, respectively an EEG wave curve representing changes of the EEG signals and a cerebral oxygen wave curve representing changes of the cerebral oxygen signals within the target period;

S102, determining whether the EEG wave curve and the cerebral oxygen wave curve satisfy a condition for controlling a controlled device to perform a target operation (the target operation may be preset according to needs of a person skilled in the art); and S103, controlling the controlled device to perform the target operation when the EEG wave curve and the cerebral oxygen wave curve satisfy the condition.

Since human brain waves change very fast and are easily affected by external factors, it is easy to cause an error or invalid operation by controlling the controlled device to perform an operation only by changes in the EEG signals. Based on this, the above control method provided by the embodiment of the present disclosure detects the EEG signals and the cerebral oxygen signals simultaneously within the target period, and generates, according to the detected EEG signals and the detected cerebral oxygen signals respectively, an EEG wave curve representing changes of the EEG signals and a cerebral oxygen wave curve representing changes of the cerebral oxygen signals within the target period, and determines whether the EEG wave curve and the cerebral oxygen wave curve satisfy a condition for controlling a controlled device to perform a target operation, and thus may avoid misoperation caused in an event of a data jump for a single wave curve or the like, improving the control accuracy. The cerebral oxygen signals are relatively stable compared to the EEG signals, and are also sensitive to changes in the brain's active state. Therefore, the combination of the two brain signals may effectively improve the control accuracy.

Specifically, the EEG signal is a voltage change generated by the ion current of the neuron when the brain is active. Sum of postsynaptic potentials that occur simultaneously in a large number of neurons forms brain waves. Changes in voltage are recorded over a period to generate brain waves (i.e., the above-described EEG wave curve). A brain wave records electrical wave changes during the activity of the brain, and is an overall reflection of the electrophysiological activity of the brain's nerve cells on the cerebral cortex or the surface of the scalp. When the brain is active and has concentrated attention, the frequency of changes in brain waves is relatively high, and the frequency of changes in brain waves decreases as the attention drops to the calm state of the brain.

Cerebral oxygen signals are usually monitored using infrared detection equipment. Different tissues of the brain have different absorption and scattering characteristics for the near-infrared spectrum. The absorption of infrared light by the brain produces a local response according to local changes in functional activity. When the brain is in an active state, it causes oxygen metabolism of local brain tissue cells, which causes changes in blood oxygen concentration in the corresponding region. Therefore, by monitoring the blood oxygen state of brain tissues, the functional activities of the brain may also be evaluated. In the above control method according to the embodiment of the present disclosure, the device for detecting the cerebral oxygen signals emits infrared light in the near-infrared band to the cerebral cortex, and the infrared light is received by the optical sensor after being reflected by the cerebral cortex. The optical sensor detects the reflected infrared light, thereby determining the amount of infrared light absorbed by the brain, further determining the blood oxygen content and determining the active state of the brain.

Specifically, as the brain's workload increases, the need for oxygen also increases. In this way, during an imagination task, the blood flow and the number of hemoglobin passing through the brain tissue will increase, and the absorption of incident near-infrared light by the brain will also increase. If the absorbed light is increased, the reflected light is reduced, and the light intensity detected by the optical sensor is reduced. In this way, changes in cerebral oxygen information can be detected. In an embodiment of the present disclosure, the cerebral oxygen wave curve may be a change curve of optical signals detected by the optical sensor within the target period.

Therefore, in the above step S103, the controlled device is controlled to perform the target operation when the EEG wave curve and the cerebral oxygen wave curve satisfy the condition, and the specific corresponding cases may be as follows.

(1) It is determined that the brain is in an active state when a numerical increase amount of the EEG wave curve is greater than or equal to a first threshold and a numerical decrease amount of the cerebral oxygen wave curve is greater than or equal to a second threshold within the target period, and the controlled device is controlled to perform an operation corresponding to the active state of the brain.

It may be seen from the above description that when the brain is in an active state, the frequency of brain waves increases, and the cerebral blood oxygen content also increases, so that the intensity of infrared light detected by the optical sensor decreases. Therefore, when it is detected that the frequency increase amount of the brain wave is greater than or equal to the first threshold and the decrease amount of the infrared light intensity is greater than or equal to the second threshold, it may be determined that the brain is in an active state, and then the controlled device may be controlled to perform an operation corresponding to the active state of the brain. In practical applications, the values of the first threshold and second threshold may be set as actual needed. The active state of the brain may be at different levels, each level corresponding to one numerical range of the EEG wave curve and one numerical range of the cerebral oxygen wave curve. When it is determined that the values of the EEG wave curve and cerebral oxygen wave curve are within a numerical range corresponding to a certain level, the controlled device may be controlled to perform the corresponding operation.

(2) It is determined that the brain is in a calm state when a numerical decrease amount of the EEG wave curve is greater than or equal to a third threshold and a numerical increase amount of the cerebral oxygen wave curve is greater than or equal to a fourth threshold within the target period, and the controlled device is controlled to perform an operation corresponding to the calm state of the brain.

When the brain is in a calm state, the frequency of brain waves will decrease, and the blood oxygen content of the brain will also decrease, so that the intensity of infrared light detected by the optical sensor increases. Therefore, when it is detected that the frequency decrease amount of the brain wave is greater than or equal to the third threshold and the increase amount of the infrared light intensity is greater than or equal to the fourth threshold, it may be determined that the brain is in a calm state, and then the controlled device is controlled to perform an operation corresponding to the calm state of the brain. The third threshold and the fourth threshold may be set according to actual needs. The first threshold may be equal to the third threshold, and the second threshold may be equal to the fourth threshold, which is not limited herein.

(3) The controlled device keeps performing the currently performed operation when the numerical change amount of at least one of the EEG wave curve and the cerebral oxygen wave curve is less than the respective target threshold (the target threshold may be preset according to the needs of those skilled in the art) within the target period.

As mentioned above, since EEG signals are prone to changes and the like, an inaccurate determination may be caused due to the lack of the brain's attention. Therefore, in the above control method provided by the embodiment of the present disclosure, it is required to determine the EEG wave curve and the cerebral oxygen wave curve. If the change in the EEG wave curve is severe and the change in the cerebral oxygen wave curve is within a small range, that is, the numerical change amount of the cerebral oxygen wave curve is less than its target threshold, there is a great possibility that it is caused by unexpected fluctuations of the EEG signals. At this time, it is necessary to make the controlled device keep performing the currently performed operation to avoid the misoperation caused by the inaccuracy of the EEG signals. Similarly, when the value of the EEG wave curve does not change much while the value of the cerebral oxygen wave curve changes drastically, it is still necessary to make the controlled device keep performing the currently performed operation. Only when the EEG wave curve and the cerebral oxygen wave curve are both changed, and the amount of change satisfies the above two conditions, the controlled device can be controlled to perform the corresponding operation.

For example, the controlled device may be a remotely controlled aircraft that is controlled based on changes in brain signals. During the flight of the aircraft, if the frequency of the brain wave is reduced by 50% as the attention is reduced, in the case of only being controlled by the EEG signal, the flight may be unstable at this time, and large deceleration may cause the aircraft unable to fly or land as normal, resulting in damage to the aircraft. At this time, if EEG signals and cerebral oxygen signals are simultaneously monitored, when the frequency of the brain wave drops sharply by 50% and the cerebral oxygen wave curve does not change significantly, the aircraft may remain the current flight state and avoid the damage caused by the misoperation. Only when the frequency of the brain wave drops by 50% while the value of the cerebral oxygen wave curve increases by 50%, the aircraft can perform the corresponding operations such as landing and deceleration. The above control method according to the embodiment of the present disclosure is not limited to the control of the above-mentioned controlled device, and other controlled devices based on brain signal according to the disclosed concept of the present disclosure are also within the protection scope of the present disclosure.

Figure 2:
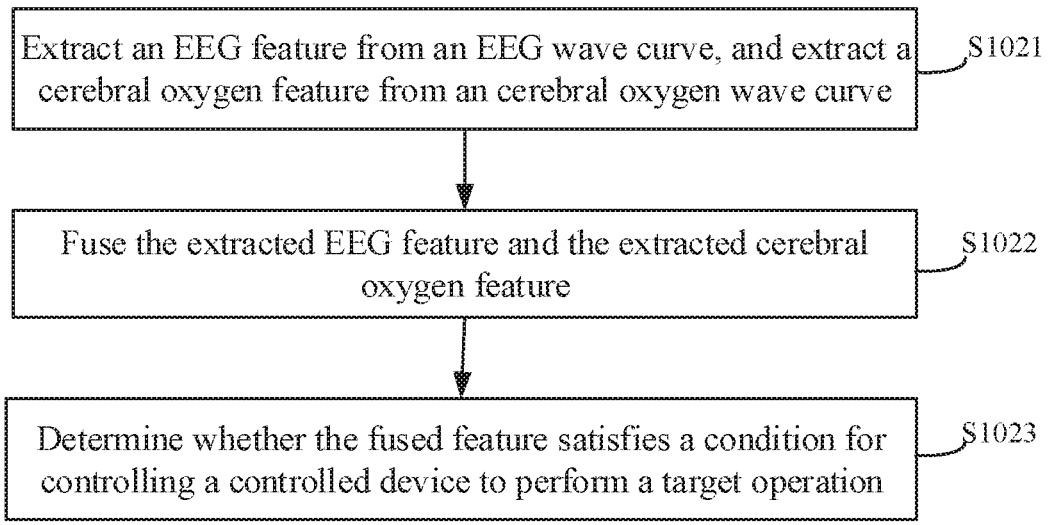
FIG. 2 is a flowchart of a control method based on brain signal according to another embodiment of the present disclosure.

In an implementable manner, as shown in FIG. 2, in the above step S102, determining whether the EEG wave curve and the cerebral oxygen wave curve satisfy the condition for controlling the controlled device to perform a target operation may specifically include the following substeps:

S1021, extracting an EEG feature from an EEG wave curve, and extracting a cerebral oxygen feature from an cerebral oxygen wave curve;

S1022, fusing the extracted EEG feature and the extracted cerebral oxygen feature; and S1023, determining whether the fused feature satisfies a condition for controlling a controlled device to perform a target operation.

In an implementation, the EEG feature of the EEG wave curve may be the corresponding relationship of the rate of change of the brain wave with time, and the cerebral oxygen feature of the cerebral oxygen wave curve may be the corresponding relationship of the rate of change of the received light intensity with time. After curve fusion, such as normalization and the like, is performed on the two time-varying curves, a threshold may be set for the fused feature. Therefore, it is determined, according to the relationship between the fused feature and the threshold, whether it satisfies the condition for controlling the controlled device to perform a target operation.

For example, the curve integral areas of the EEG wave curve and the cerebral oxygen wave curve may be calculated within a certain period, and then the calculated integral areas are taken as the features of the two wave curves. Then, the difference between the two obtained curve integral areas is calculated. It can be determined whether the condition is satisfied by comparing the difference with a set threshold, so that the controlled device can be controlled, according to the determination result, to perform a target operation corresponding to the condition. Alternatively, a segment of curve with a sharp change in the EEG wave curve and the cerebral oxygen wave curve may be intercepted as a feature, the EEG feature curve and the cerebral oxygen feature curve are weighted and linearly fitted to obtain a new curve equation, the curve equation is compared with the set threshold or target condition to determine whether the condition is satisfied. When the condition is satisfied, the controlled device is controlled to perform a corresponding operation. For another example, the derivative function of the EEG wave curve and of the cerebral oxygen wave curve may be obtained separately, and the extremum of each of the two derivative functions may be extracted and compared with a set threshold to determine whether the condition for controlling the controlled device to perform a corresponding operation is satisfied. In practical applications, the determination may be performed by any of the above methods according to the actual determination accuracy and the determination condition.

Compared to the manner in which a controlled device is controlled based on only EEG signals in the prior art, the control method based on brain signal according to the embodiment of the present disclosure simultaneously detects EEG signals and cerebral oxygen signals, generates an EEG wave curve and a cerebral oxygen wave curve, and determines whether the EEG wave curve and the cerebral oxygen wave curve satisfy the condition for controlling the controlled device to perform a target operation. In this way, misoperation caused in the event of a change in data of a single wave curve or the like may be avoided, improving control accuracy.

Figure 3:
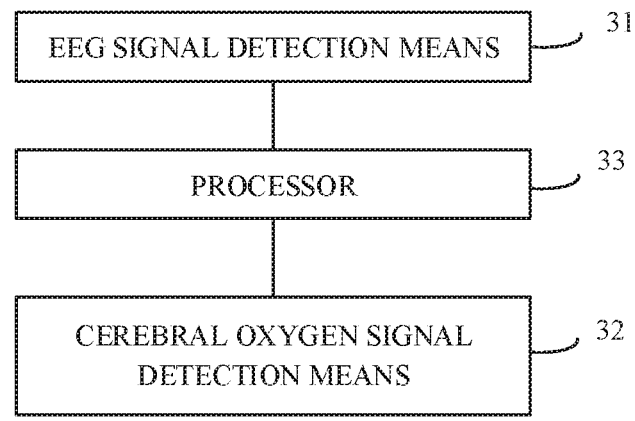
FIG. 3 is a schematic structural diagram of a brain signal monitoring device according to an embodiment of the present disclosure.

Based on the same concept of the disclosure, an embodiment of the present disclosure provides a control device based on brain signal, which has a structure as shown in FIG. 3. The control device includes an EEG signal detection apparatus 31, a cerebral oxygen signal detection apparatus 32, and a processor 33. The EEG signal detection apparatus 31 and the cerebral oxygen signal detection apparatus 32 are coupled to the processor 33 respectively.

According to an embodiment of the present disclosure, the processor 33 is configured to control the EEG signal detection apparatus 31 to periodically detect EEG signals and control the cerebral oxygen signal detection apparatus 32 to periodically detect cerebral oxygen signals within the target period, generate, according to the detected EEG signals and the detected cerebral oxygen signals respectively, an EEG wave curve representing changes of the EEG signals and a cerebral oxygen wave curve representing changes of the cerebral oxygen signals within the target period, determine whether the EEG wave curve and the cerebral oxygen wave curve satisfy a condition for controlling a controlled device to perform a target operation, and when it is determined that the EEG wave curve and the cerebral oxygen wave curve satisfy the condition, send a control instruction to the controlled device, so that the controlled device performs a target operation corresponding to the control instruction.

The control device based on brain signal according to the embodiment of the present disclosure detects the EEG signals and the cerebral oxygen signals simultaneously, generates an EEG wave curve and a cerebral oxygen wave curve, and determines whether the EEG wave curve and the cerebral oxygen wave curve satisfy the condition for controlling the controlled device to perform a target operation. In this way, misoperation caused in the event of changes in data of a single wave curve or the like can be avoided, improving the accuracy of the control device.

According to the embodiment of the present disclosure, the control device may control a controlled device to perform the target operation when the EEG wave curve and the cerebral oxygen wave curve satisfy the condition, and the specific actions may include:

(1) determining that, within the target period, a brain is in an active state when a numerical increase amount of the EEG wave curve is greater than or equal to a first threshold and a numerical decrease amount of the cerebral oxygen wave curve is greater than or equal to a second threshold, controlling the controlled device to perform an operation corresponding to the active state of the brain.

(2) determining that, within the target period, the brain is in a calm state when a numerical decrease amount of the EEG wave curve is greater than or equal to a third threshold and a numerical increase amount of the cerebral oxygen wave curve is greater than or equal to a fourth threshold, controlling the controlled device to perform an operation corresponding to the calm state of the brain.

(3) keeping the controlled device performing, within the target period, the currently performed operation when a numerical change amount of at least one of the EEG wave curve and the cerebral oxygen wave curve is less than the respective target threshold.

Figure 4:
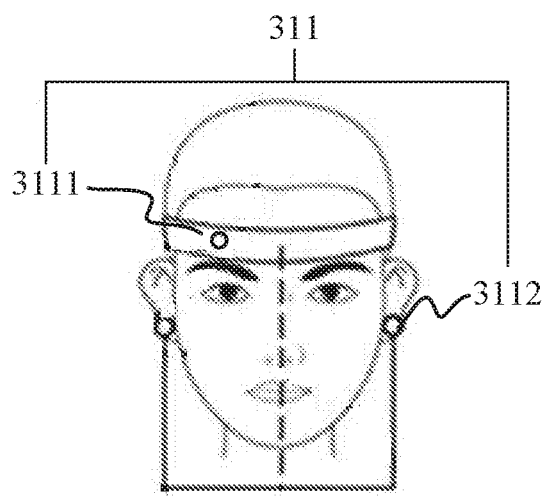
FIG. 4 is a schematic structural diagram of an EEG signal detection apparatus according to an embodiment of the present disclosure.

Further, the EEG signal detection apparatus 31 includes an EEG detection electrode 311. By causing the EEG detection electrode 311 to contact a scalp, the potential change generated by brain nerve cells can be recorded. Among them, an electrode placed at a zero potential is referred to as a reference electrode, and an electrode placed at a non-zero potential is referred to as a working electrode. The reference electrode and the working electrode are coupled respectively to the processor by, for example, a wire, thereby amplifying a potential difference between the working electrode and the reference electrode. Specifically, as shown in FIG. 4, the EEG detection electrode 311 may include a working electrode 3111 and a reference electrode 3112, wherein the working electrode 3111 is placed on the scalp, and the reference electrode 3112 is placed on the earlobe. As the EEG signals have characteristics of strong noise background, being weak at low frequency (0.1~70 Hz, a input 1/f voltage noise of a low frequency band amplifier is large), high internal resistance, electrode polarization potential instability, etc., the front-end voltage follower should also have properties of high common mode rejection ratio, low input 1/f, low voltage noise, low input current noise, and drift feature. In order to reduce the output impedance and reduce the interference to the lead induction power frequency, a silver chloride powder electrode may be used to reduce polarization potential and improve the stability of the polarization potential.

Figure 5:
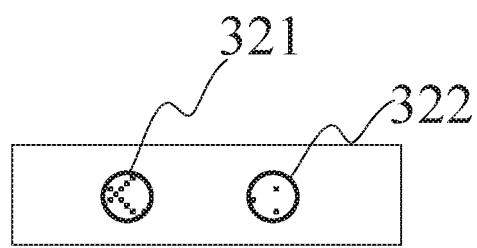
FIG. 5 is a schematic structural diagram of a cerebral oxygen signal detection apparatus according to an embodiment of the present disclosure.

In a specific application, in the above control device according to the embodiment of the present disclosure, as shown in FIG. 5, the cerebral oxygen signal detection apparatus includes a detection light source 321 and an optical sensor 322 spaced apart from the detection light source 321 by a target distance (the target distance may be preset according to the needs of a person skilled in the art).

The detection light source 321 may be configured to emit infrared light to the cerebral cortex, so that the emitted infrared light interacts with the blood oxygen tissue of the cerebral cortex.

The optical sensor 322 is configured to detect the infrared light that has been reflected by the cerebral cortex without interacting with blood oxygen tissues.

Figure 6:
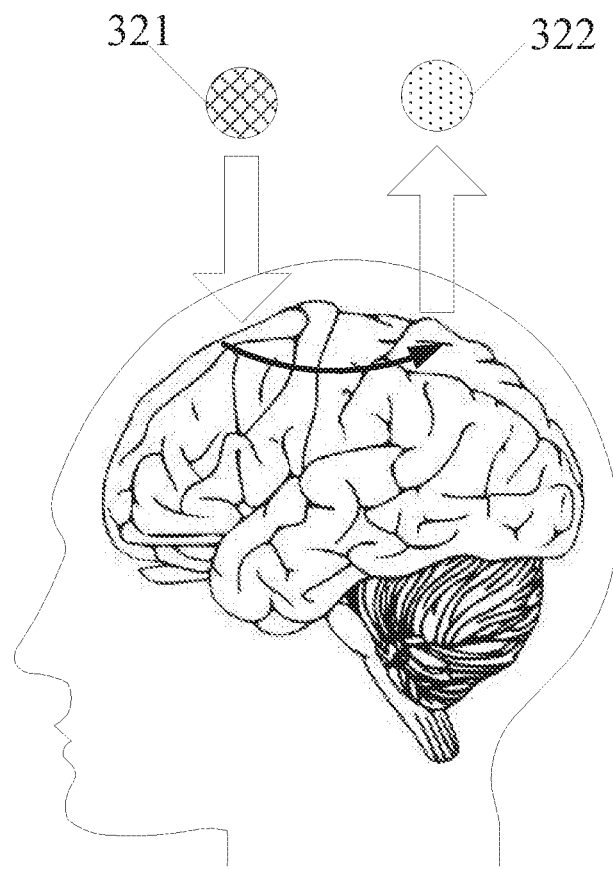
FIG. 6 is a schematic diagram illustrating the principle of a cerebral oxygen signal detection apparatus according to an embodiment of the present disclosure.

In practical applications, the detection light source 321 is generally a radiation source. In the embodiment of the present disclosure, the detection light source 321 adopts a near-infrared light source, and the near-infrared light source does not damage human health compared to the radiation source. Moreover, as the near-infrared spectroscopy has obvious influence on blood flow, it is more suitable for the detection of the cerebral oxygen signals. The principle for detection of the cerebral oxygen signals as described above is based on the absorption of near-infrared light by brain tissue blood flow and hemoglobin. As shown in FIG. 6, the detection light source 321 emits light in the near-infrared band to the cerebral cortex, and hemoglobin in the tissue related to the blood oxygen state in the cerebral cortex reflects the cerebral oxygen content, which has an absorption effect on the near-infrared light, and thus the light detected by the optical sensor 322 is the infrared light that is not absorbed by the brain and is reflected back. Then the lost part of the infrared light is absorbed by hemoglobin, and thus the state of blood oxygen in the brain may be indirectly reflected by the optical sensor. The state of blood oxygen in the brain is also positively correlated with the activity degree of the brain, and thus an association may be established between the intensity of the detected infrared light with the degree of activity of the brain. In the embodiment of the present disclosure, the cerebral oxygen signal is the intensity of infrared light that is negatively correlated with blood oxygen in the brain.

In practical applications, the infrared light used by the detection light source 321 may generally penetrate a certain depth to reach the cortex, so that blood oxygen information is detected and reflected to the optical sensor 322. However, it is generally difficult for infrared light to pass through the entire head from the forehead and be detected at the posterior occipital region, and thus a reflective detection method is employed in the embodiment of the present disclosure. In addition, it should be noted that since the light emitted by the detection light source 321 has an influence on the light intensity detection of the optical sensor 322, it is required to remain a target distance between the detection light source 321 and the optical sensor 322, so that the light emitted by the detection light source 321 is not directly received by the optical sensor 322, which affects the detection result. In an embodiment, the distance between the detection light source 321 and the optical sensor 322 may be set between 2-4 cm. The optical sensor 322 may employ an optical probe. For example, the optical probe is composed of a silicon tube (PD tube), a transimpedance amplifier, a light guiding fiber, a filter, a spring case, and the like. By using a transimpedance amplifier front-end design, it can overcome the defects of motion noise introduced easily by traditional fiber optic probes. A 650 nm long-wavelength filter may be employed, such that external light interference can be suppressed and photocurrent noise of the PD tube can be reduced.

In the above control device according to the embodiment of the present disclosure, the principles for detection of the EEG signals and the cerebral oxygen signals are different, and the detections of the two kinds of brain signals do not interfere with each other. The two kinds of brain signals may be collected simultaneously and synchronously by separate devices, and the collected EEG signals and the collected cerebral oxygen signals are both related to the activity degree of the brain. Therefore, it may improve the accuracy of determination of the active state of the brain by using two types of data.

Figure 7:
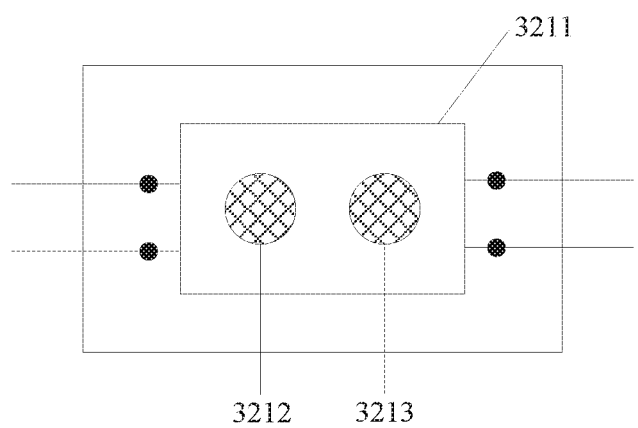
FIG. 7 is a schematic structural diagram of a detection light source according to an embodiment of the present disclosure.
Figures 8A, 8B, 8C:
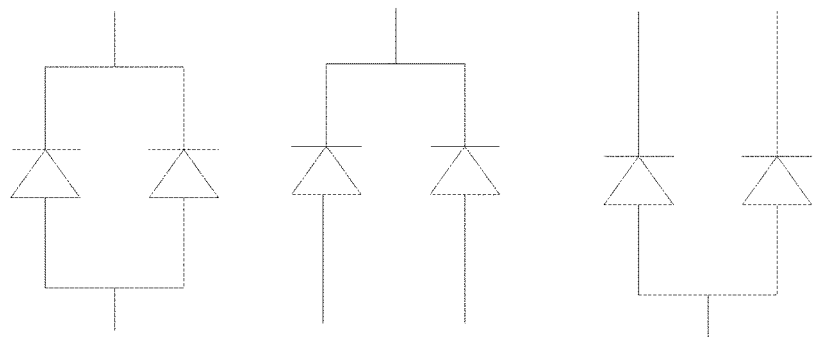
FIGS. 8A-8C are schematic diagrams of coupling of a detection light source according to an embodiment of the present disclosure.

Further, in the above-described cerebral oxygen signal detection apparatus according to the embodiment of the present disclosure, as shown in FIG. 7, the detection light source 321 includes a first light emitting chip 3212 and a second light emitting chip 3213 which are packaged in the same package structure 3211. As biological tissues (including cerebral cortex tissues) have high scattering and low absorption properties toward infrared light in the near-infrared band (650-950 nm), near-infrared light may detect the cerebral cortex area at a depth of 2-3 cm below the scalp with a high spatial resolution. Hemoglobin, in turn, has a strong absorption of light in the band, and therefore, two light emitting chips are employed in the embodiments of the present disclosure. The light emitted by the first light emitting chip 3212 has a wavelength of about 760 nm and a half-wave width of about 20 nm. The light emitted by the second light emitting chip 3213 has a wavelength of about 850 nm and a half-wave width of about 35 nm. The two light emitting chips mentioned above may be light emitting diodes. The two light emitting diodes may adopt three coupling manners as shown in FIGS. 8A-8C. In FIGS. 8A-8C, FIG. 8A shows a coupling manner in which two light emitting diodes are connected in parallel, FIG. 8B shows a coupling manner in which two light emitting diodes have a common cathode, and FIG. 8C shows a coupling manner in which two light emitting diodes have a common anode. When two light emitting chips are simultaneously packaged in the same package structure, it is not necessary to separately fabricate two light source structures. By adopting the above-mentioned multi-wavelength integral light source, not only the volume of the light source can be optimized, but also the influence of ordinary discrete light source tubes on the detection result due to the discrete spatial positions thereof can be sufficiently eliminated.

Figure 9:
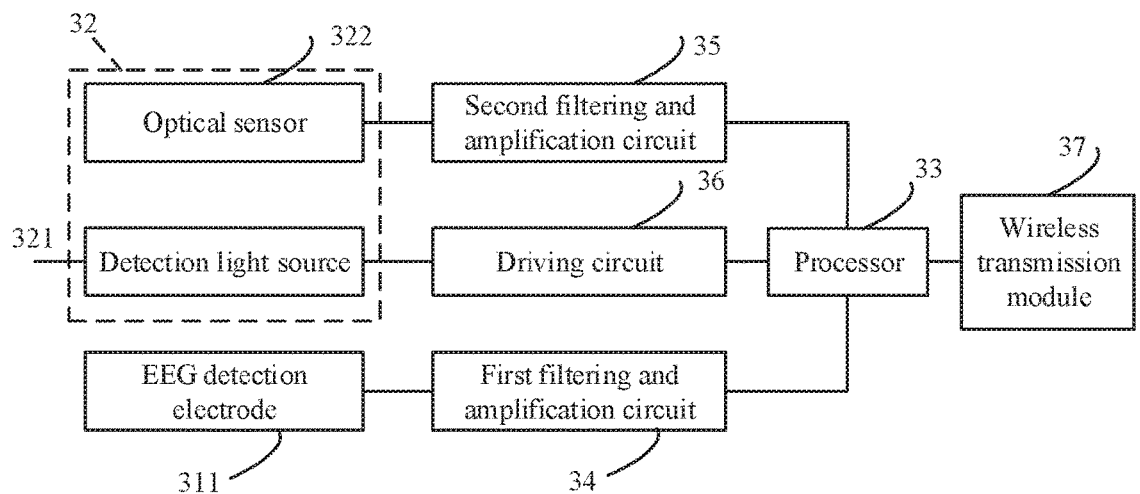
FIG. 9 is a schematic structural diagram of a brain signal monitoring device according to another embodiment of the present disclosure.

The above control device according to the embodiment of the present disclosure, as shown in FIG. 9, further includes a first filtering and amplification circuit 34 coupled between the processor 33 and the EEG detection electrode 311, and a second filtering and amplification circuit 35 coupled between the processor 33 and the optical sensor 322. Since the EEG signals detected by the EEG detection electrode 311 and the optical sensor 322 and the light intensity signal related to the cerebral oxygen signals have large background noise, the filtering and amplification circuits may perform filtering processing on the two signals and optimize the signals as needed, to form an effective EEG wave curve and cerebral oxygen wave curve.

Further, as shown in FIG. 9, the above control device according to the embodiment of the present disclosure further includes a driving circuit 36 coupled to the detection light source 321. In practical applications, the driving circuit 36 is mainly composed of an operational amplifier NPN transistor current feedback resistor, and may convert a voltage carrier signal into four 5 to 15 mA current carrier signals, to drive the dual-wavelength detection light source 321. The analog front end may be an ADS1299 chip from TI company and includes eight input multiplexers, a low noise programmable gain amplifier, and a synchronous sampling 24-bit analog-to-digital converter. Under the condition of 12 times gain and 70 Hz bandwidth, the equivalent input voltage noise is less than 1.0, which satisfies medical EEG signal collection requirements.

In addition, as shown in FIG. 9, the foregoing control device according to the embodiment of the present disclosure further includes a wireless transmission module 37 configured to transmit a control instruction from the processor 33 to the controlled device. The wireless transmission module 37 may adopt EMW3162 with the highest network data transmission rate of 20 Mbps, and has a 128 k SRAM buffer, which may satisfy real-time data transmission requirements. The wireless transmission module 37 has a built-in microcontroller STM32F205RG, which may directly program modules to realize the functions of analog front-end communication light source carrier generation and Wi-Fi network communications, and so on.

The above control device according to the embodiment of the present disclosure further includes a power module (not shown) for supplying power to components, such as, a corresponding near-infrared illumination driving circuit, a filtering amplification circuit for optically acquired signals, and a filtering and amplification circuit for the output of the EEG detection electrode. The power module may include a charging circuit that may charge a single lithium battery using a 5V DC power supply, and may raise the voltage of the single lithium battery to 6V using a DC-DC boost power supply. With two kinds of low-dropout linear voltage regulator circuits, the EEG signals and cerebral oxygen signals can be filtered and amplified, and then outputted to a data collection module (not shown). The data collection module may transmit the collected data to a device such as a computer with processor 33 in a wireless or wired manner through a wireless communication module for wireless transmission or a USB port. The power module also provides low-noise analog power to a DAC module built in the wireless transmission module. A 2.5V precision power supply reference is combined with a voltage follower to provide a low noise virtual ground.

Figure 10:
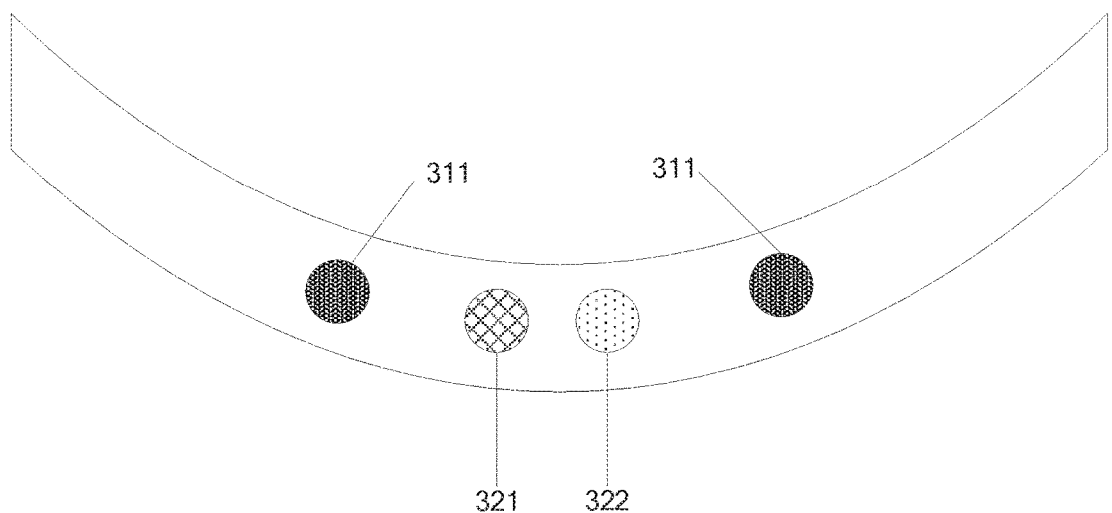
FIG. 10 is a schematic structural diagram of a headset component according to an embodiment of the present disclosure.

In a specific implementation, the above control device according to the embodiment of the present disclosure is integrated in a headset component as shown in FIG. 10. The headset component may be a sports bandage or a helmet or the like. The detection light source 321 and the optical sensor 322 may correspond to the position of the forehead of the head. The two EEG detection electrodes 311 are located on both sides for detecting the EEG signals. When motion imagination happens in the brain, the EEG signals and the cerebral oxygen signals will change accordingly. The brain's EEG signals are generated under the cerebral cortex and collected by the EEG detection electrode. The EEG signals are amplified by the first filtering and amplification circuit, and then sent to the data collection module (such as a data acquisition card). The cerebral oxygen signals are also sent to the data collection module after being processed by the second filtering and amplification circuit. After that, the data is transmitted to the processor 13 through the communication module, and an EEG wave curve and a cerebral oxygen wave curve are generated by the processor 13. The control device determines whether the EEG wave curve and the cerebral oxygen wave curve satisfy the condition for controlling the controlled device to perform a target operation. At last, a control instruction can be generated to control the controlled device to perform the corresponding operation.

On the other hand, an embodiment of the present disclosure further provides a human-machine interaction device, including any of the above-described control device based on brain signal and the controlled device. The controlled device may be various types of controlled devices that are controlled based on brain signals. For example, the controlled device may be the above-described remote control aircraft or the like according to an embodiment of the present disclosure, which is not specifically limited herein.

The brain signal control method and device and the human-machine interaction device according to the embodiments of the present disclosure, periodically acquire EEG signals and cerebral oxygen signals within a target period, generate, according to the acquired EEG signals and cerebral oxygen signals respectively, an EEG wave curve representing changes of the EEG signals and a cerebral oxygen wave curve representing changes of the cerebral oxygen signals within the target period, determine whether the EEG wave curve and the cerebral oxygen wave curve satisfy a condition for controlling a controlled device to perform a target operation, and control the controlled device to perform the target operation when the EEG wave curve and the cerebral oxygen wave curve satisfy the condition. The above control method provided by the embodiments of the present disclosure simultaneously detects EEG signals and cerebral oxygen signals, generates an EEG wave curve and a cerebral oxygen wave curve, determines whether the EEG wave curve and the cerebral oxygen wave curve satisfy a condition for controlling a controlled device to perform a target operation, and may prevent the controlled device from executing misoperation in the event of a jump in data of a single wave curve or the like, improving control accuracy.

While the embodiments of the present disclosure have been described, those skilled in the art may make further changes and modifications to these embodiments as they know the basic inventive idea. Therefore, the appended claims are intended to be interpreted as including example embodiments and all the changes and modifications falling within the scope of the present disclosure.

It will be apparent to those skilled in the art that various modifications and variations may be made to the present disclosure without departing from the spirit and scope of the disclosure. Thus, if these modifications and variations of the present disclosure fall within the scope of the claims of the present disclosure and their equivalent technologies, the present disclosure is also intended to include these changes and variations.

What is claimed is:

1. A control method based on brain signals, the method comprising:
    periodically acquiring electroencephalogram (EEG) signals and cerebral oxygen signals within a target period and generating, according to the acquired EEG signals and cerebral oxygen signals, respectively an EEG wave curve representing changes of the EEG signals and a cerebral oxygen wave curve representing changes of the cerebral oxygen signals within the target period;
    determining whether the EEG wave curve and the cerebral oxygen wave curve satisfy a condition for controlling a controlled device to perform a target operation; and
    controlling the controlled device to perform the target operation when the EEG wave curve and the cerebral oxygen wave curve satisfy the condition;
    wherein determining whether the EEG wave curve and the cerebral oxygen wave curve satisfy a condition for controlling the controlled device to perform a target operation comprises:
        extracting an EEG feature from the EEG wave curve and extracting a cerebral oxygen feature from the cerebral oxygen wave curve, wherein the EEG feature is a corresponding relationship of a rate of change of a brain wave with time, and the cerebral oxygen feature is a corresponding relationship of a rate of change of a received light intensity with time;
        fusing the extracted EEG feature and the extracted cerebral oxygen feature by performing curve fusion on the EEG wave curve and the cerebral oxygen wave curve; and
        determining whether the condition for controlling the controlled device to perform the target operation is satisfied, according to a relationship between the fused feature and a threshold.

2. The method according to claim 1, wherein controlling the controlled device to perform the target operation when the EEG wave curve and the cerebral oxygen wave curve satisfy the condition comprises:
    determining that, within the target period, a brain is in an active state when a numerical increase amount of the EEG wave curve is greater than or equal to a first threshold and a numerical decrease amount of the cerebral oxygen wave curve is greater than or equal to a second threshold, and controlling the controlled device to perform an operation corresponding to the active state of the brain; or
    determining that, within the target period, the brain is in a calm state when a numerical decrease amount of the EEG wave curve is greater than or equal to a third threshold and a numerical increase amount of the cerebral oxygen wave curve is greater than or equal to a fourth threshold, and controlling the controlled device to perform an operation corresponding to the calm state of the brain.

3. The method according to claim 1, wherein controlling the controlled device to perform the target operation when the EEG wave curve and the cerebral oxygen wave curve satisfy the condition further comprises:
    within the target period, keeping the controlled device performing the operation which is currently performed when a numerical change amount of at least one of the EEG wave curve and the cerebral oxygen wave curve is less than respective target thresholds.

4. A control device based on brain signal, comprising an electroencephalogram (EEG) signal detection apparatus, a cerebral oxygen signal detection apparatus, and a processor, wherein the EEG signal detection apparatus and the cerebral oxygen signal detection apparatus are coupled to the processor respectively;
    the processor is configured to i) control the EEG signal detection apparatus to periodically detect EEG signals and control the cerebral oxygen signal detection apparatus to periodically detect cerebral oxygen signals within a target period, ii) generate, according to the detected EEG signals and the detected cerebral oxygen signals, an EEG wave curve representing changes of the EEG signals and a cerebral oxygen wave curve representing changes of the cerebral oxygen signals within the target period respectively, iii) determine whether the EEG wave curve and the cerebral oxygen wave curve satisfy a condition for controlling a controlled device to perform a target operation, and iv) in response to determining that the EEG wave curve and the cerebral oxygen wave curve satisfy the condition, send a control instruction to the controlled device to cause the controlled device to perform a target operation corresponding to the control instruction;

wherein determining whether the EEG wave curve and the cerebral oxygen wave curve satisfy a condition for controlling the controlled device to perform a target operation comprises:

extracting an EEG feature from the EEG wave curve and extracting a cerebral oxygen feature from the cerebral oxygen wave curve, wherein the EEG feature is a corresponding relationship of a rate of change of a brain wave with time, and the cerebral oxygen feature is a corresponding relationship of a rate of change of a received light intensity with time;

fusing the extracted EEG feature and the extracted cerebral oxygen feature by performing curve fusion on the EEG wave curve and the cerebral oxygen wave curve; and determining whether the condition for controlling the controlled device to perform the target operation is satisfied, according to a relationship between the fused feature and a threshold.

5. The control device according to claim 4, wherein the controlled device performing the target operation corresponding to the control instruction when the EEG wave curve and the cerebral oxygen wave curve satisfy the condition comprises:

determining that, within the target period, a brain is in an active state when a numerical increase amount of the EEG wave curve is greater than or equal to a first threshold and a numerical decrease amount of the cerebral oxygen wave curve is greater than or equal to a second threshold, and controlling the controlled device to perform an operation corresponding to the active state of the brain; or determining that, within the target period, the brain is in a calm state when a numerical decrease amount of the EEG wave curve is greater than or equal to a third threshold and a numerical increase amount of the cerebral oxygen wave curve is greater than or equal to a fourth threshold, and controlling the controlled device to perform an operation corresponding to the calm state of the brain; or keeping the controlled device performing, within the target period, the currently performed operation when a numerical change amount of at least one of the EEG wave curve and the cerebral oxygen wave curve is less than respective target thresholds.

6. The control device according to claim 5, wherein the control device is integrated in a headset component.

7. The control device according to claim 4, wherein the EEG signal detection apparatus comprises an EEG detection electrode.

8. The control device according to claim 7, further comprising a first filtering and amplification circuit coupled between the processor and the EEG detection electrode.

9. The control device according to claim 8, wherein the control device is integrated in a headset component.

10. The control device according to claim 7, wherein the control device is integrated in a headset component.

11. The control device according to claim 4, wherein the cerebral oxygen signal detection apparatus comprises a detection light source, and an optical sensor spaced apart from the detection light source by a target distance, wherein the detection light source is configured to emit infrared light to cerebral cortex so that the emitted infrared light interacts with the blood oxygen tissue of the cerebral cortex, and wherein the optical sensor is configured to detect the infrared light that has been reflected by the cerebral cortex without interacting with the blood oxygen tissue.

12. The control device according to claim 11, wherein the detection light source comprises a first light emitting chip and a second light emitting chip which are packaged in a same package structure, wherein a wavelength of infrared light emitted by the first light emitting chip is 760 nm, and wherein a wavelength of infrared light emitted by the second light emitting chip is 850 nm.

13. The control device according to claim 11, further comprising a second filtering and amplification circuit coupled between the processor and the optical sensor.

14. The control device according to claim 11, further comprising a driving circuit coupled to the detection light source.

15. The control device according to claim 11, wherein the control device is integrated in a headset component.

16. The control device according to claim 4, further comprising a wireless transmission module configured to send the control instruction from the processor to the controlled device.

17. The control device according to claim 16, wherein the control device is integrated in a headset component.

18. The control device according to claim 4, wherein the control device is integrated in a headset component.

19. A human-machine interaction device, comprising a control device and a controlled device according to claim 4.

* * * * *